United States Patent
McAmish et al.

(10) Patent No.: US 6,235,659 B1
(45) Date of Patent: May 22, 2001

(54) MEDICAL LINEN WITH REGIONALLY IMPRINTED PERFORMANCE AREAS

(75) Inventors: Larry McAmish, Mooresville, NC (US); Raymond Barbuto, Dagsboro, DE (US); Jeffrey Taylor, Arlington, TX (US); Alex Laurie, Royston (GB)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/207,541

(22) Filed: Dec. 8, 1998

Related U.S. Application Data

(60) Provisional application No. 60/067,938, filed on Dec. 8, 1997.

(51) Int. Cl.[7] ............ B32B 27/04; B32B 27/12; B32B 5/02

(52) U.S. Cl. ............ 442/79; 442/85; 442/86; 2/114

(58) Field of Search ............ 442/79, 85, 86; 2/114

(56) References Cited

U.S. PATENT DOCUMENTS

| | | |
|---|---|---|
| 2,668,294 | 2/1954 | Gilpin . |
| 3,490,072 * | 1/1970 | Keltner ............ 2/114 |
| 3,669,106 | 6/1972 | Schrading et al. . |
| 3,803,640 * | 4/1974 | Ericson ............ 2/114 |
| 3,868,728 | 3/1975 | Krzewinski . |
| 4,171,542 * | 10/1979 | Cox et al. ............ 2/51 |
| 4,504,977 | 3/1985 | King et al. . |
| 4,605,401 * | 8/1986 | Chmelier et al. ............ 604/368 |
| 4,612,673 * | 9/1986 | Underhill ............ 2/114 |
| 5,271,100 * | 12/1993 | Holt ............ 2/114 |
| 5,398,700 * | 3/1995 | Mills et al. ............ 128/853 |
| 5,414,867 * | 5/1995 | Bowling et al. ............ 2/51 |
| 5,444,871 | 8/1995 | Lopez . |
| 5,513,401 * | 5/1996 | Abe et al. ............ 5/451 |
| 5,567,478 * | 10/1996 | Houben et al. ............ 427/342 |
| 5,673,433 | 10/1997 | Rothrum . |
| 5,813,052 * | 9/1998 | Taylor ............ 2/114 |

FOREIGN PATENT DOCUMENTS

| | | |
|---|---|---|
| 166 124 | 1/1986 | (EP) . |
| 497 608 | 8/1992 | (EP) . |
| 0691203 | 1/1996 | (EP) . |
| 2296216 | 6/1996 | (GB) . |
| 2728280 | 6/1996 | (FR) . |

* cited by examiner

Primary Examiner—Elizabeth M. Cole
Assistant Examiner—Arti R. Singh
(74) Attorney, Agent, or Firm—Andrew C. Farmer

(57) ABSTRACT

A medical gown and drape are disclosed in which regions thereof are imprinted with performance enhancing coatings. The gown has regions in the chest and sleeve areas imprinted with a liquid repellent coating to protect the wearer from fluids. The drape preferably has an absorbent or super absorbent coating surrounding a fenestration through which an operation may occur. The drape may also have regions coated with water repellent or friction enhancing materials. The gown further has adhesive closures rather than ties.

10 Claims, 15 Drawing Sheets

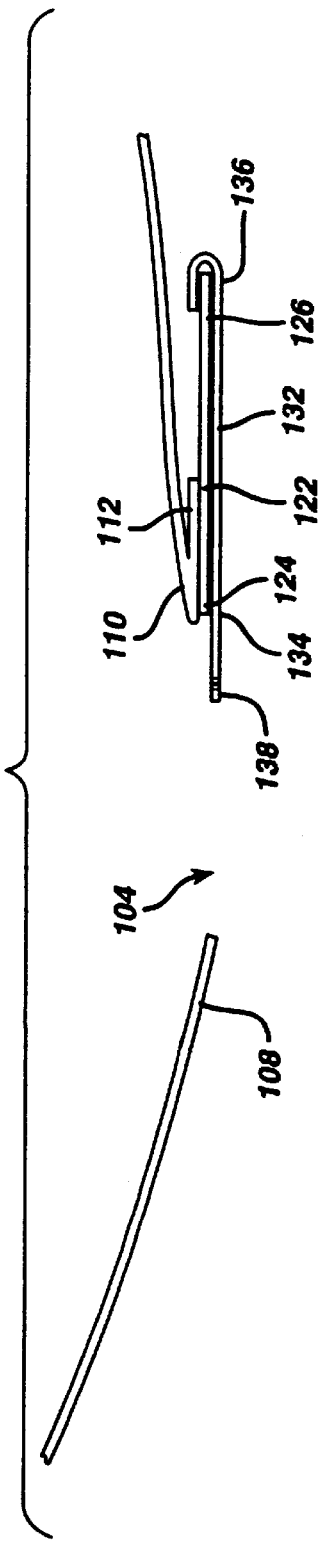
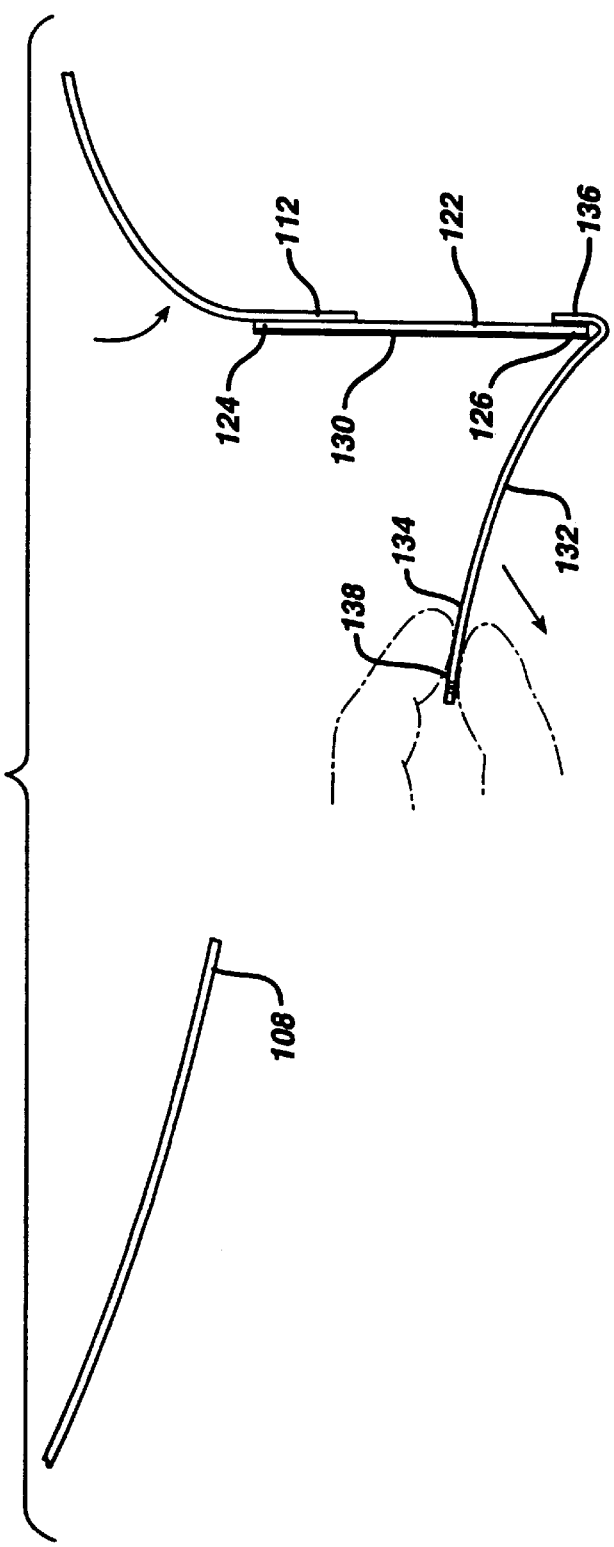
FIG. 16
FIG. 17

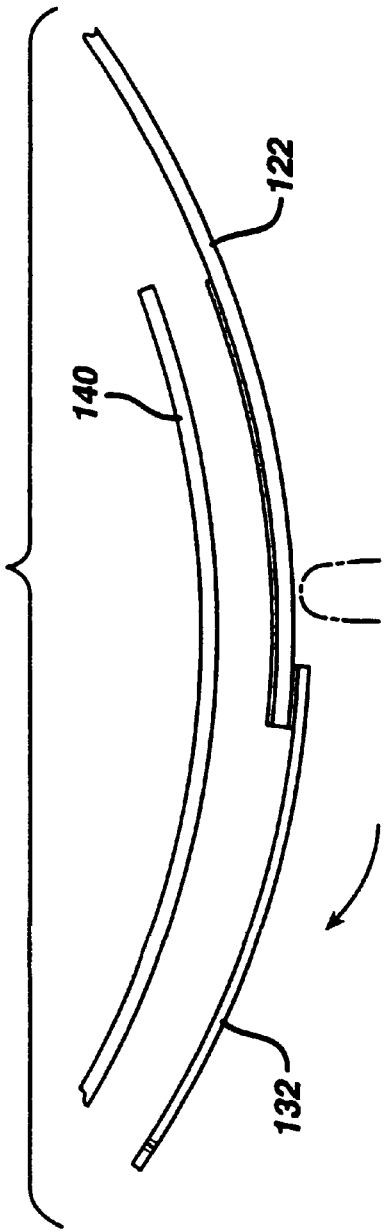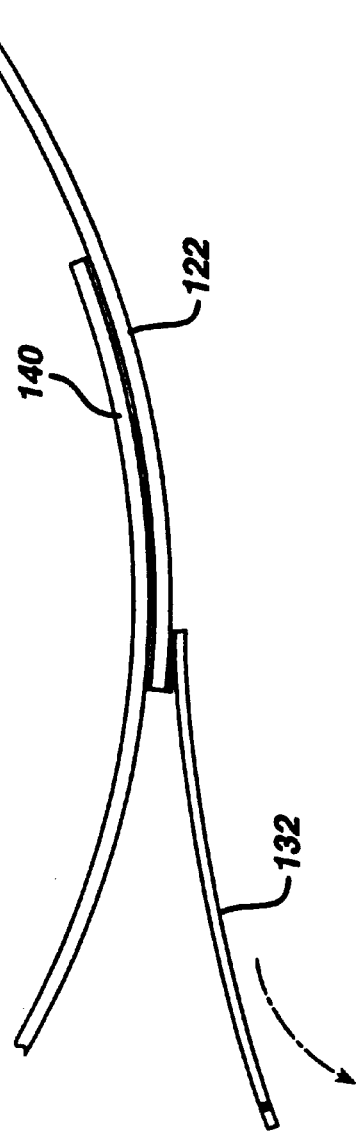

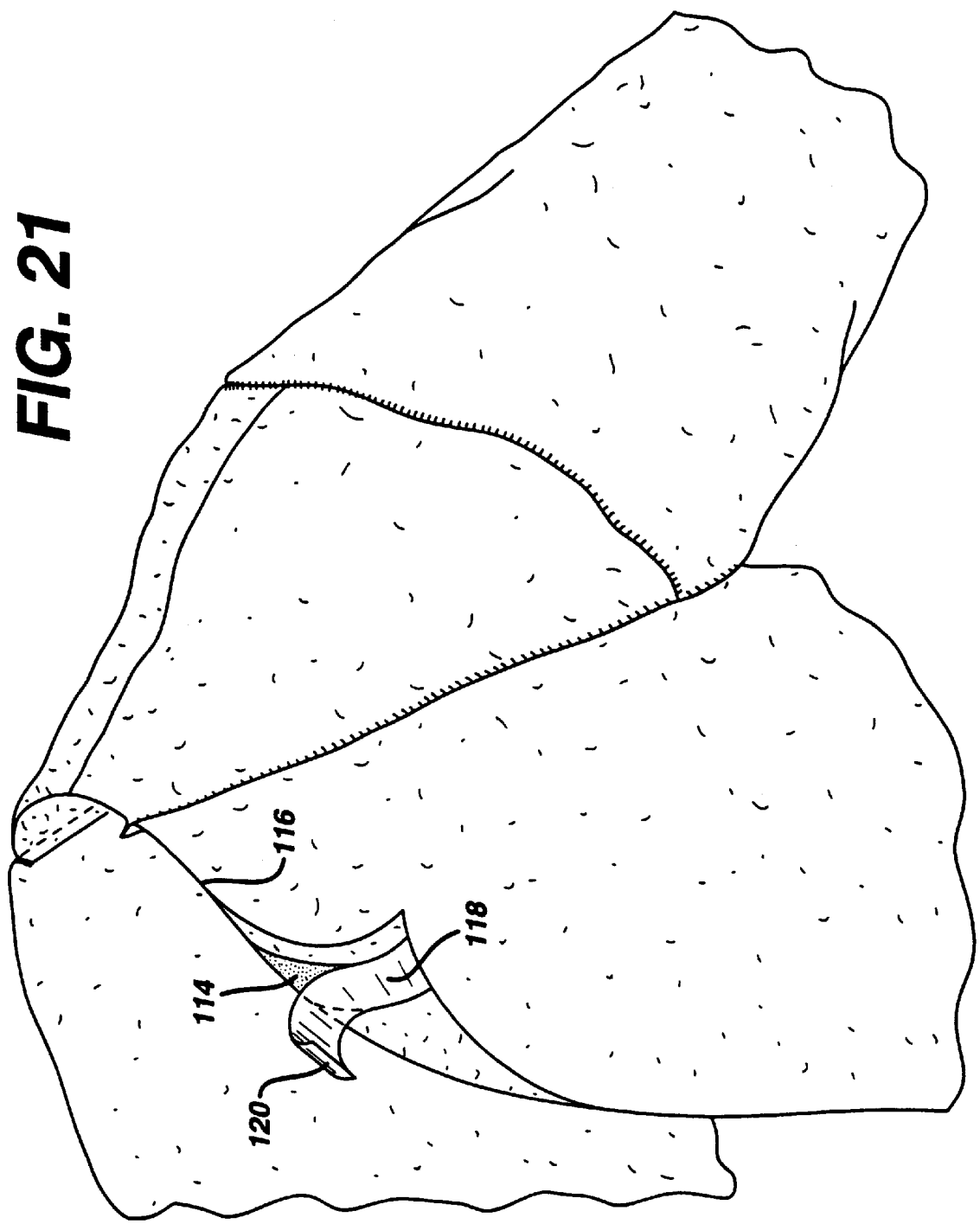

MEDICAL LINEN WITH REGIONALLY IMPRINTED PERFORMANCE AREAS

This application claims the benefit of U.S. Provisional Application No. 60/067,938 filed Dec. 8, 1997.

THE FIELD OF THE INVENTION

The present invention relates to medical linens, such as drapes and gowns, and more particularly to medical linens having regions thereon imprinted with performance enhancing materials.

BACKGROUND OF THE INVENTION

Medical linens, such as drapes and gowns, are intended to protect both the patients and medical personnel from microbial contamination. The patient is protected from germs in the atmosphere or on the medical personnel and the medical personnel are protected from the patients bodily fluids which make contain harmful infectious agents, such as the virus which causes AIDS. Some medical linens are reusable and constructed from sturdy fabrics such as woven cotton which can be washed and sterilized repeatedly. Other such linens are disposable, and are constructed from less expensive fabrics such as nonwoven materials. Suitable examples for each are well known in the art.

When constructing a medical gown to be worn by a medical professional during surgery or other medical procedures in which bodily fluids may be present, several methods are currently known to provide fluid imperviousness in the areas of the gown exposed to bodily fluids. If the gown is constructed of panels which are sewn together, as most such gowns are, those panels requiring repellency can be formed from a water repellent material such as a plastic film. Alternately, to improve comfort such panels may be provided with a laminated construction comprising a layer of a nonwoven fabric or other comfortable material and a second layer of repellent film. As is shown in the Lopez U.S. Pat. No. 5,444,871 issued Aug. 29, 1995, the King et al. U.S. Pat. No. 4,504,977 issued Mar. 19, 1985 and the Rothrum U.S. Pat. No. 5,673,433 issued Oct. 7, 1997, each of which are incorporated herein by reference, films of repellent material may be applied to local regions such as the sleeves or chest of the medical gown.

Similarly, medical drapes that are used to cover a patient during a medical procedure generally require material having highly absorbent properties and frequently high liquid repellent properties. To increase comfort to the patient and decrease cost of the drape, such drapes are frequently constructed with such properties limited to specific regions of the drape. Heretofore, this has been accomplished with panels or laminations of absorbent and fluid repellent materials only at the specific areas requiring such absorbency and repellency.

For instance in a drape intended for a surgical procedure, the drape is draped over the patient and the procedure is typically performed through a fenestration through the drape. The drape is typically provided with some form of reinforcement at the fenestration for added physically integrally, and also with an area of increased absorbency. For instance, the drape may cover the entire patient but bodily fluids may only be present at a small location adjacent the fenestration. In such instance a panel of absorbent material may be laminated to the drape surrounding the fenestration to keep that area of the drape free from puddled liquids.

Where large quantities of liquid may be present, a fluid repellent lamination may be provided to direct the fluid away from the fenestration to a location where it can be captured and disposed of properly. This may be combined with the absorbent panel. The other presently known alternative to providing laminated construction to provide these regional performance characteristics is to construct the gown from panels attached together at their edges, with the separate panels having differing performance characteristics, such as high absorbency.

It can be cumbersome to construct a gown or drape with local areas of laminations. Likewise, it can be cumbersome to construct a gown or drape employing different materials for the different panels in a multi-panel construction. When employing different materials, to achieve highly localized performance characteristics, the design of the gown frequently requires additional panels or a more complicated construction to provide the fluid repellent materials in specific locations. When applying laminations, it can be difficult to accurately align the laminated material. The present invention overcomes these and other limitations in the prior art.

SUMMARY OF THE INVENTION

A medical linen according to the present invention comprises a fabric substrate; and a coating printed on one or more regions of the substrate, the coating modifying a performance characteristic of the fabric substrate.

The medical linen preferably comprises either a medical gown or a medical drape. The substrate preferably comprises a nonwoven fabric. The coating can increase the liquid repellency of the substrate, increase the friction of the substrate, or enhance the liquid absorbing capacity of the substrate.

The medical gown preferably comprising a body covering portion and sleeves extending from the body portion to terminate in cuffs, wherein the one or more regions comprises a central operative area of said body covering portion and further comprises portions of the sleeves adjacent the cuffs. Preferably, the coating is liquid impervious. It can comprise polyvinylchloride plastisol. Additionally, the gown may further comprise one or more areas coated with a repellency enhancing material to raise the repellency in these areas to at least 20 cm of static head.

The medical drape preferably has a fenestration therethrough, with the coating being water absorbent positioned adjacent the fenestration. Preferably, such coating comprises an acrylic acid based super absorbent material.

A method for making a medical linen having a fabric substrate with a region having differing performance characteristics than the substrate comprising the step of applying and adhering a fluid substance to the region to form a coating thereon, the coating having a differing performance characteristic from the substrate.

BRIEF DESCRIPTION OF THE FIGURES

FIGS. 16 to 19 are sectional views through a waist closure of the gown of FIG. 15, showing its operation;

FIG. 21 is a detail in perspective view a neck closure on the gown of FIG. 15.

DETAILED DESCRIPTION

Figure 1:
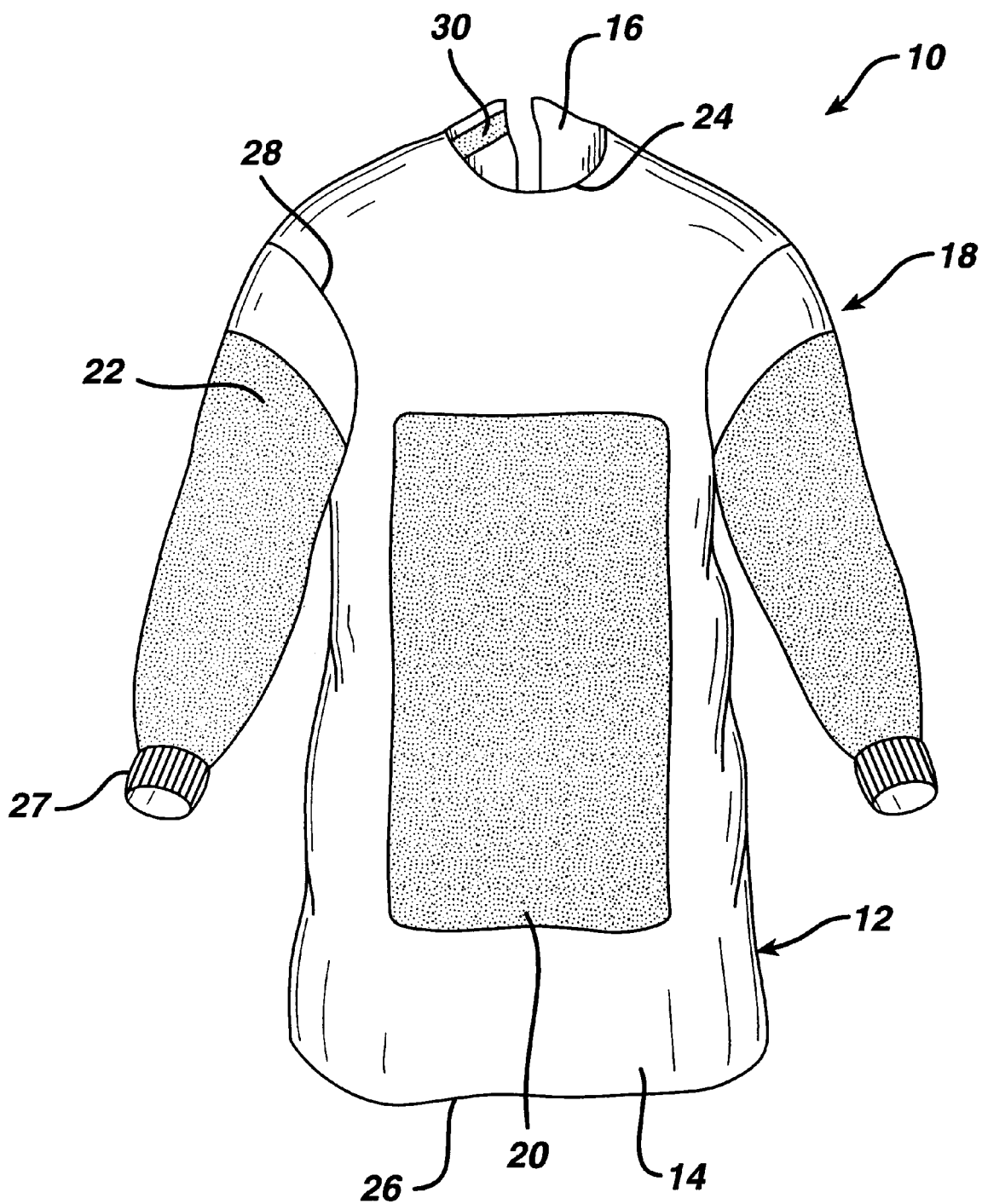
FIG. 1 is a front elevational view of a gown according to the present invention.

FIG. 1 illustrates a medical gown 10 according to the present invention. It comprises a body 12 having a front portion 14 and back portion 16 and a pair of sleeves 18. The body and sleeves are formed of a suitable nonwoven material to provide a disposable gown; however, a reusable fabric such as cotton, polyester and blends thereof may also be employed. Preferably such material is breathable allowing transpiration of air and water vapor to improve the comfort of the wearer. Suitable fabrics include polyester-wood pulp hydro-entangled nonwovens treated with fluorocarbons to enhance repellency, such as FABRIC 450, from Johnson & Johnson Medical, Inc. and SONTARA available from DuPont. The back portion 16 may be formed of less substantial and untreated fabrics. For instance, the front portion 14 preferably exhibits a repellency of between 20 and 30 cm static head, most preferably about 25 cm, but the back portion 16 can be less than 20, and preferably about 10 to lower cost and enhance overall breathability of the gown.

AATCC Test Method 127-1989 measures the resistance of fabrics to the penetration of water under static pressure, with the water column being measured in centimeters. Test specimens are mounted under the orifice of a conical well and are subjected to water pressure increasing at a constant rate (1 cm/sec) until three points of leakage occur through the fabric. The ASTM Emergency Standard 21 and 22 define imperviousness for medical gowns. One side of a test sample of fabric is exposed to synthetic blood medium (with a bacteriaphage for method 22). Pressure is applied across the test sample of the fabric on the following schedule: 5 minutes at atmospheric pressure (on both sides of the fabric), one minute with 2 psi applied to the fluid side of the fabric, the other side remaining at atmospheric pressure, followed by 54 minutes with both sides at atmospheric pressure.

A coating of impervious material is applied to a chest area 20 and to sleeve areas 22. The chest coating 20 generally need not necessarily extend up to a neck 24 or down to a lower edge 26 of the gown 10, but broader coverage with the coating 20 provides enhanced protection. It should extend laterally to cover a frontal portion of a wearer's body (not shown). The gown 10 in FIG. 1 is shown in a somewhat open configuration prior to being donned by a wearer and it would be expected that when so donned the chest coating. 20 would cover laterally the frontal area of a wearer's body. The sleeve coatings 22 extend from a cuff 27 up toward a shoulder seam 28 where the sleeves 18 join the gown body 12 however, the sleeve coating 22 need not extend all the way to the shoulder seam 28. The precise location of the chest coating and sleeve coatings 22 can be manipulated by those of skill in the art to meet the particular needs of a given gown or surgical procedure for which it is intended.

Preferably, the liquid impervious coatings 20 and 22 are provided by coating a liquid repellent material, such as a film-forming polymer, selectively to areas of the fabric substrate, then drying the polymer to form a coherent film on the fabric substrate impervious to liquid. Preferably the coatings 20 and 22 are applied prior to the gown being sewed or otherwise assembled together, but they could be applied after the gown is constructed. The preferred application method would be determined primarily by the throughput requirement, the coating weight desired and cost. Preferably a doctor blade, air knife, reverse rollercoating, or rotary screen printing process is employed. Each of these methods is capable of depositing coating weights in the range of 50 to 200 microns. Most preferably a rotary screen printing method is employed as it most easily can deposit the coating in a desired pattern. Such a process will be described hereinafter with respect to FIG. 15.

There are many film forming polymer systems capable of providing impervious barriers to body fluids. A suitable polymer should be selected on the basis of its ability to be cast from solution, its flexibility after the coating is dried and its cost. A preferred material is polyvinylchloride plastisol which has a high solids content (greater than 95%) which limits the cost of treating solvent emissions released during the drying and curing process. Other suitable coatings include latex, especially synthetic latexes, polyurethanes, polyetherurethanes, polyethylenes, and polypropylenes. In any event, the coated fabric should be impervious to bodily fluids.

Figure 2:
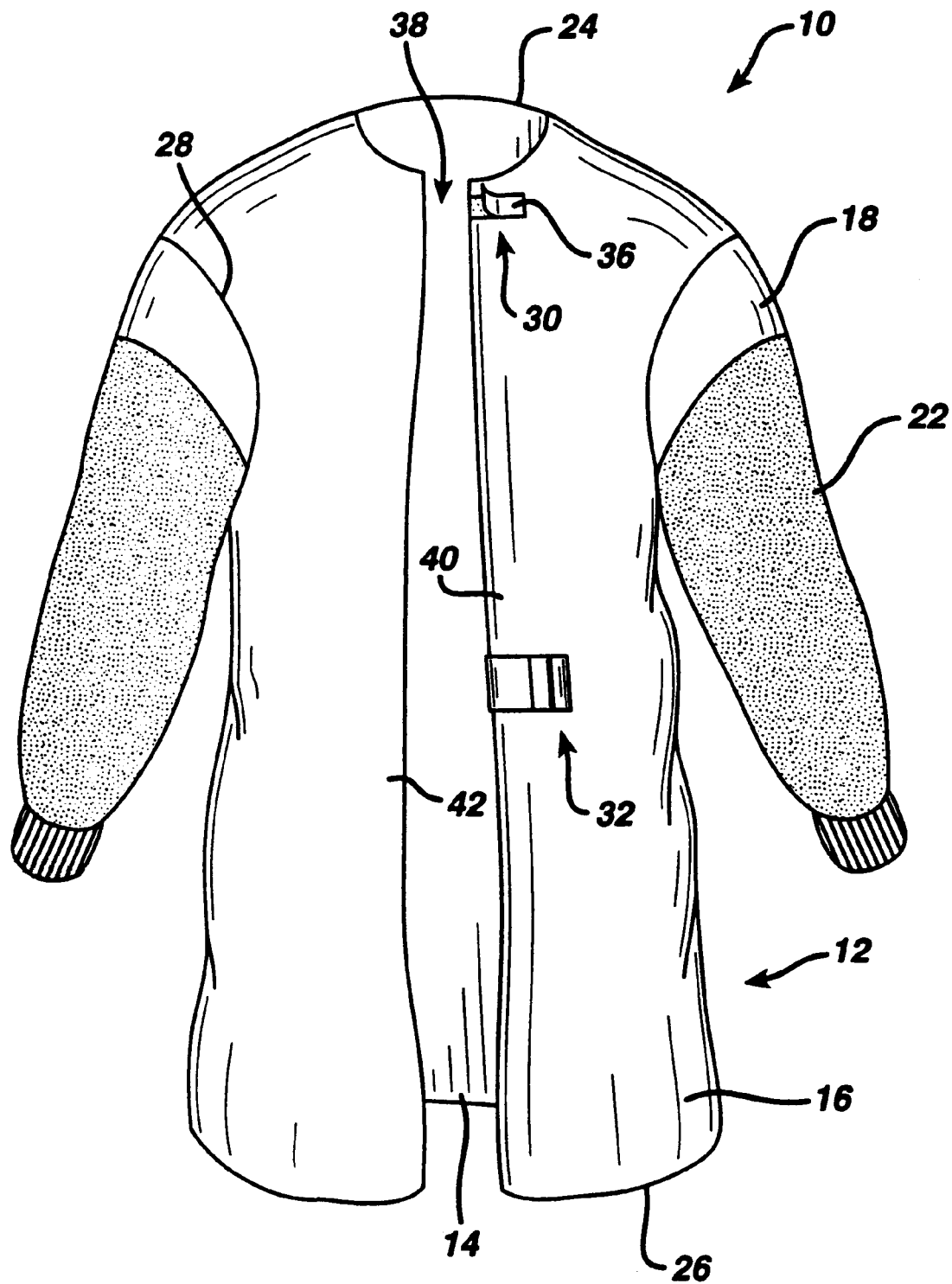
FIG. 2 is a rear elevational view of the gown of FIG. 1.

FIG. 2 shows the back of the gown 10 and a taped type neck closure 30 and waist closure 32. The neck closure 30 comprises a tab coated with an adhesive and overlaid with a release liner 36, such as siliconized paper. To adhere the neck closre 30, the release liner 36 is removed and the tab is folded over and attached to the gown back 16. Alternatively, an area of the gown back 16 at the neck 24 may be coated with an adhesive and have a release liner (not shown in FIG. 2) attached thereover. Closure can then be effected by removing the release liner and adhering the two sides of the gown back 16 together at the adhesive.

Figure 3:
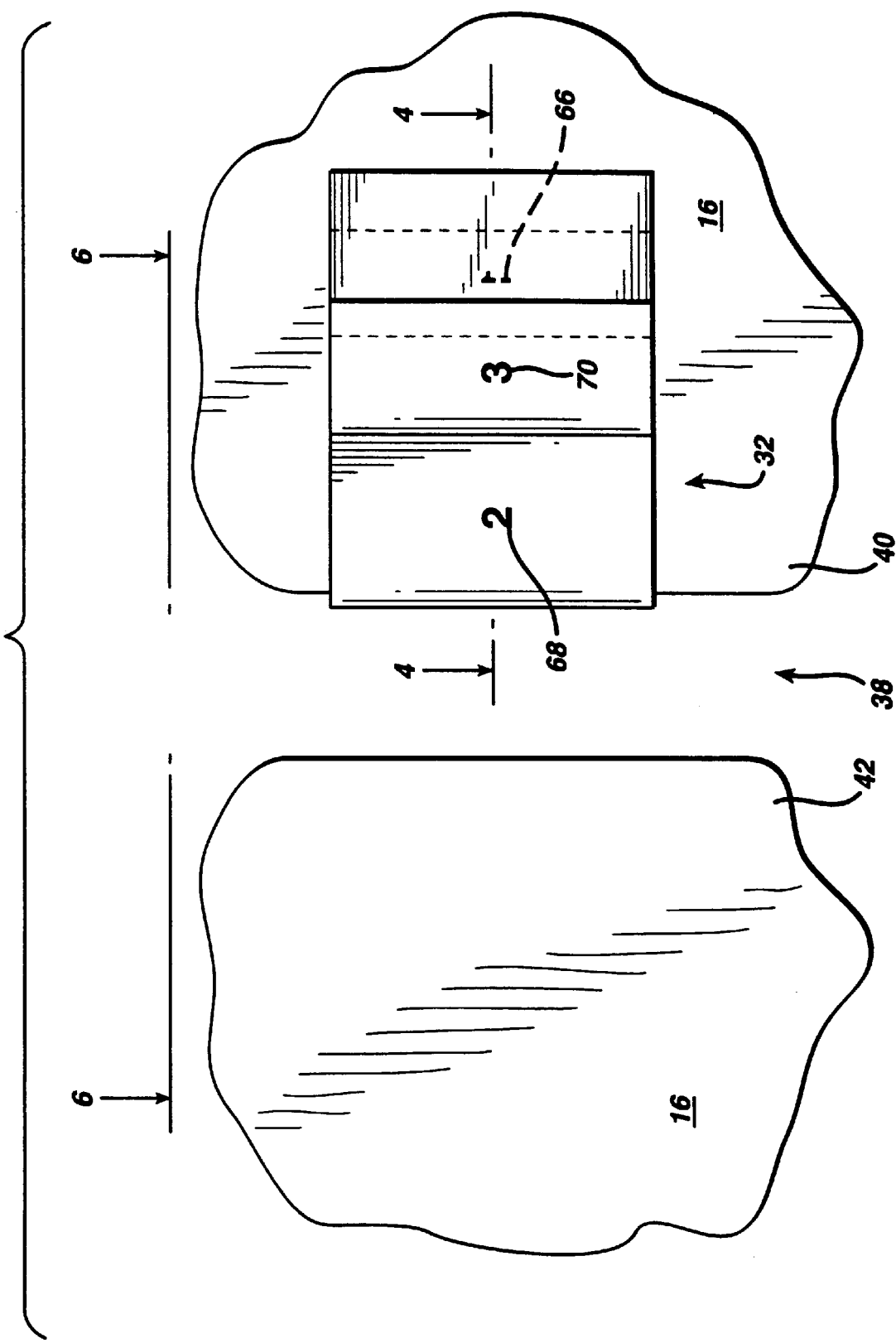
FIG. 3 is a sectional view taken along lines 3—3 of FIG. 2, illustrating a gown closure.
Figure 4:
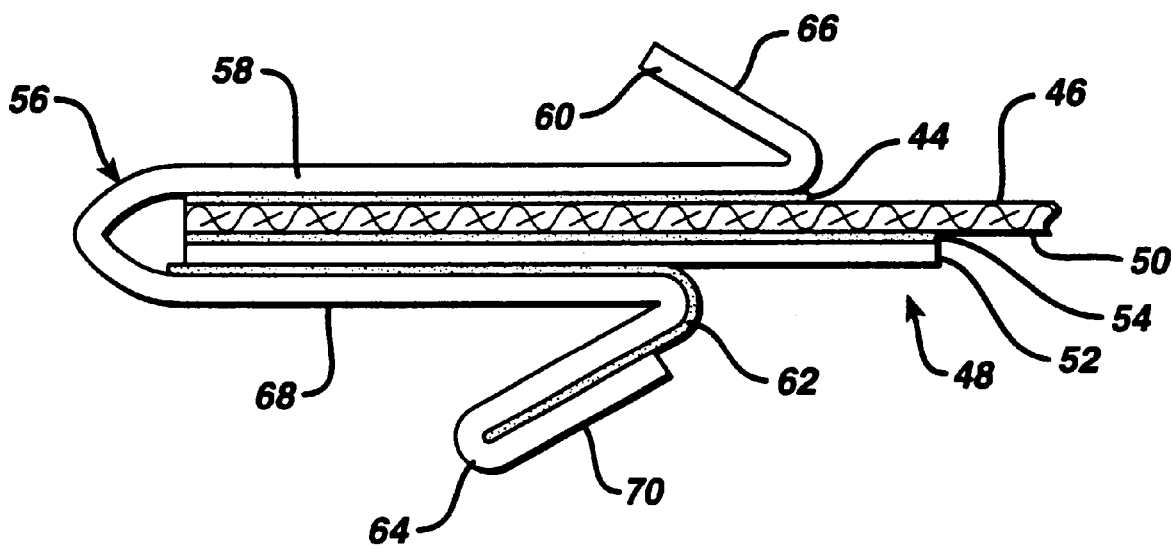
FIG. 4 is a sectional view taken along lines 4—4 of FIG. 3.
Figure 5:
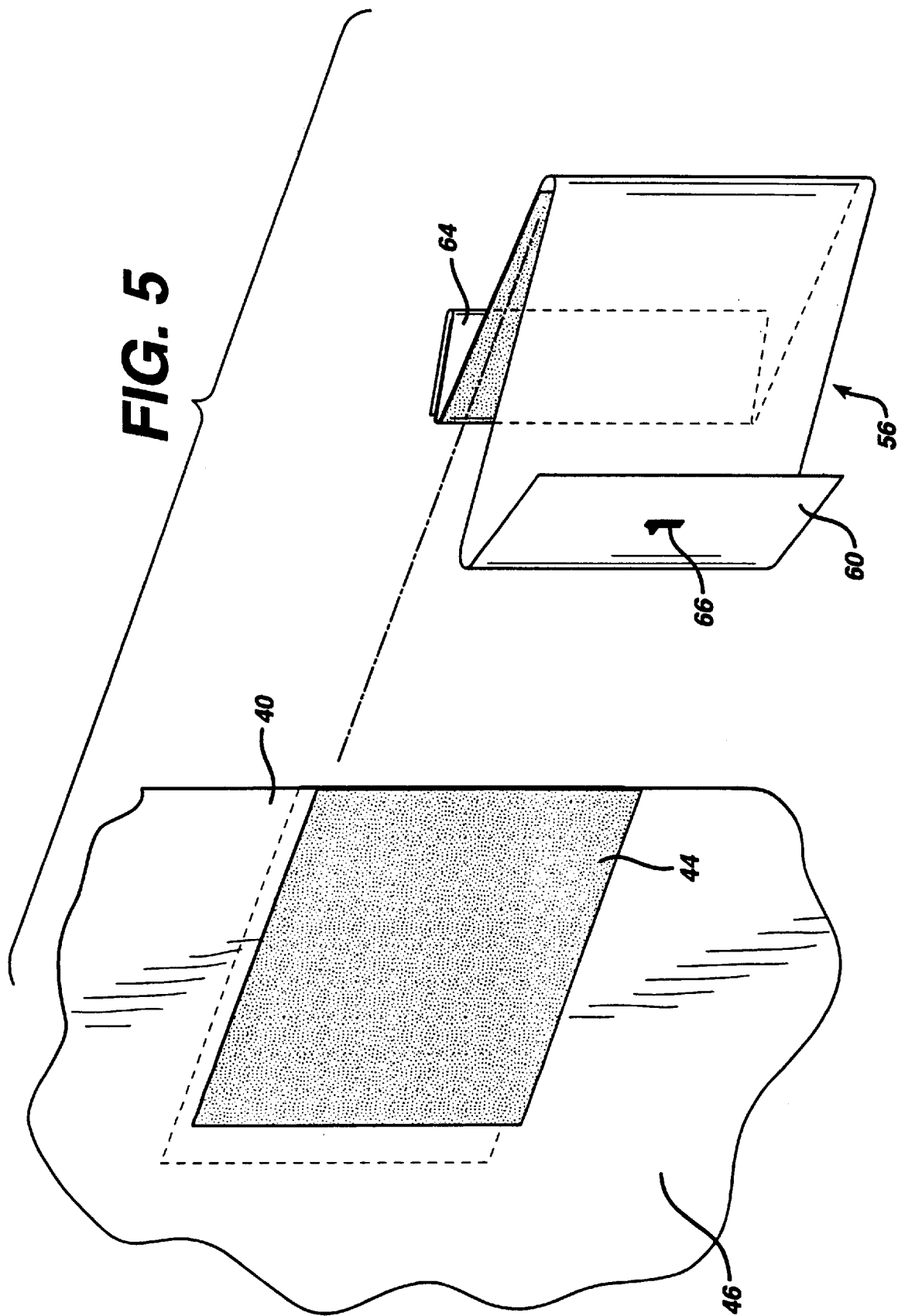
FIG. 5 is a partially exploded perspective view of the closure of FIG. 3.
Figure 6:
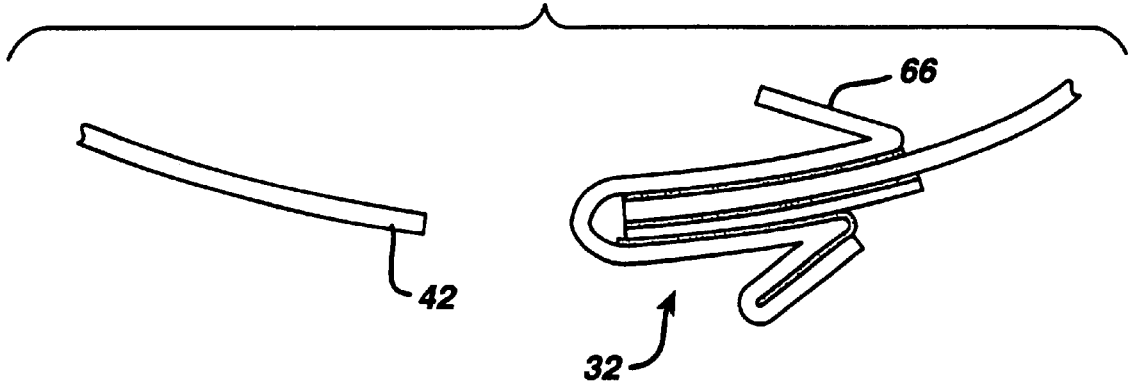
FIG. 6 is a sectional view taken along lines 6—6 of FIG. 3.

Turning also to FIGS. 3 to 5, the waist closure 32 is illustrated in more detail. opening 38 in the back 16. A first edge 40 and second edge 42 are connected to each other to effect closure. The waist closure 32 comprises a first adhesive layer 44 on an inside surface 46 of the gown back 16 at the first edge 40. A release material 48 is applied to an opposite surface 50 in registry with the first adhesive layer 44. The release surface 48 may comprise a release liner 52 adhered to the outside surface 50 with an adhesive 54. A special release strip 56 covers the first adhesive layer 44 and aids in applying the waist closure 32 in a sterile fashion. The release strip 56 is formed of a long strip of release liner 58 having one end thereof folded over to form a tab 60. From the tab 60 the release liner 58 extends across the first adhesive layer 44, and round the first edge 40. Adhesive 62 on the release liner 58 adheres to the release surface 48 on the outside surface 50. The release liner 58 terminates in a bi-fold tab 64 wherein the release liner first folds away from the release surface 48 and then back upon itself to cover the adhesive 62.

The release strip 56 bears indicia to indicate the steps in the sterile application of the waist closure 32. For instance, the tab 60 bears an indicia 66, such as the numeral "1", indicating that the first step in the application of the waist closure 32 is to pull the tab 60 and release the release strip 56 from the first adhesive layer 44. A second indicia 68, such as the numeral "2", appears on the release strip where it covers the release surface 48 and a third indicia 70, such as the numeral "3", appears on the bi-fold tab 64.

Figure 7:
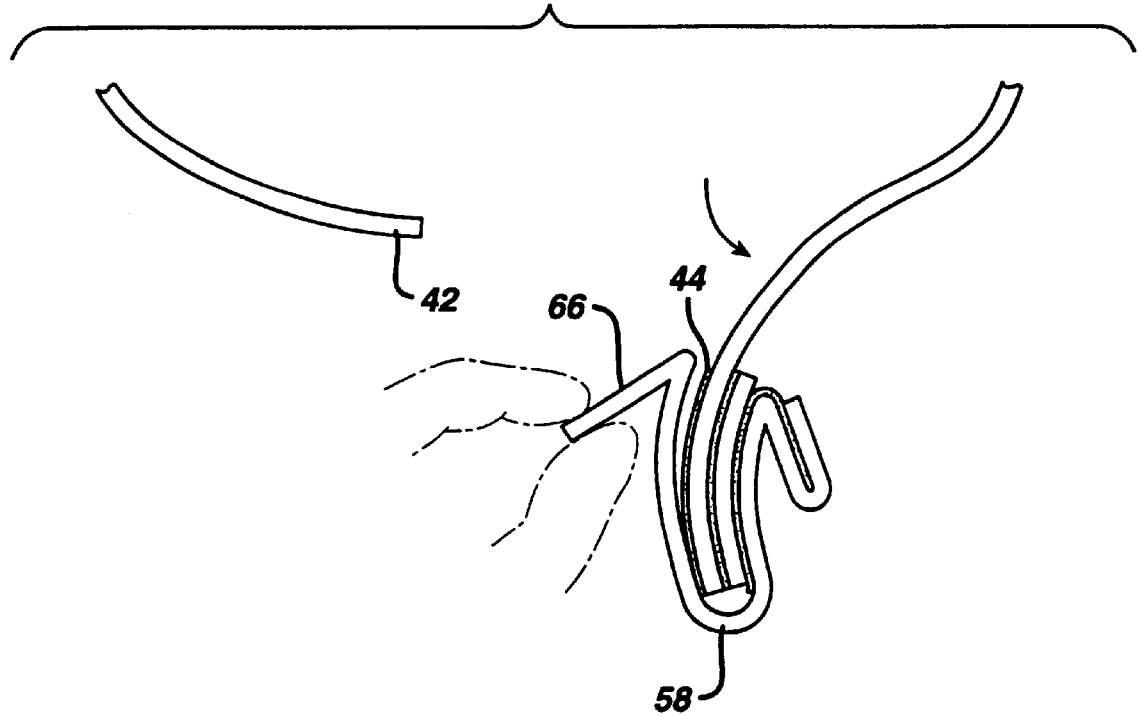
FIGS. 7 to 10 are sectional views similar to FIG. 6 illustrating operation of the closure.
Figure 8:
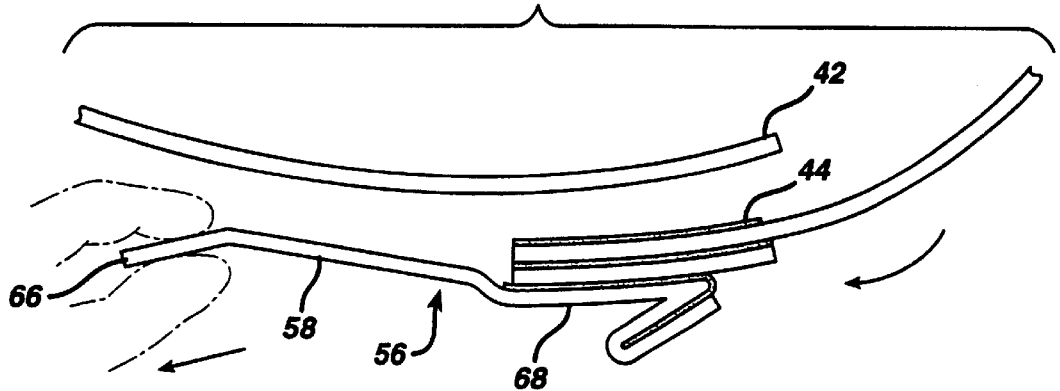
Figure 9:
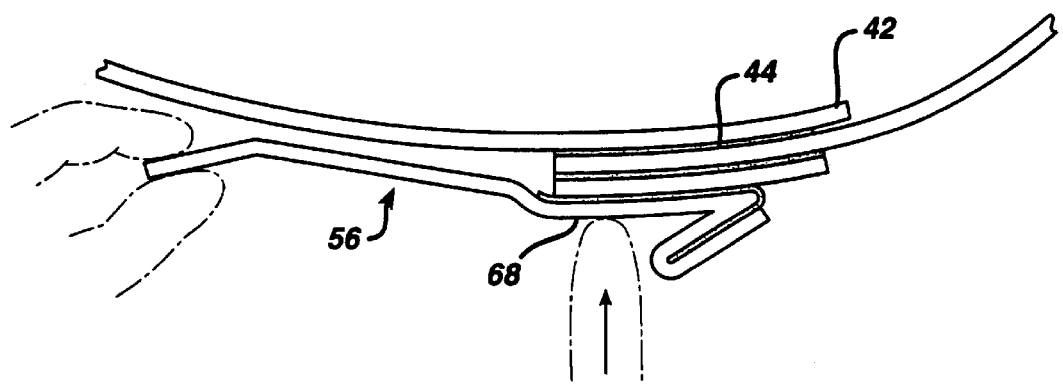
Figure 10:
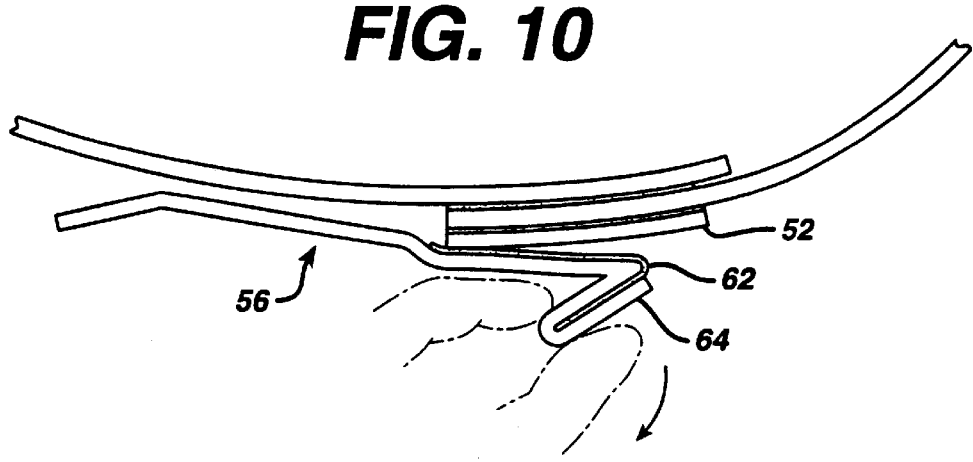
Figure 11:
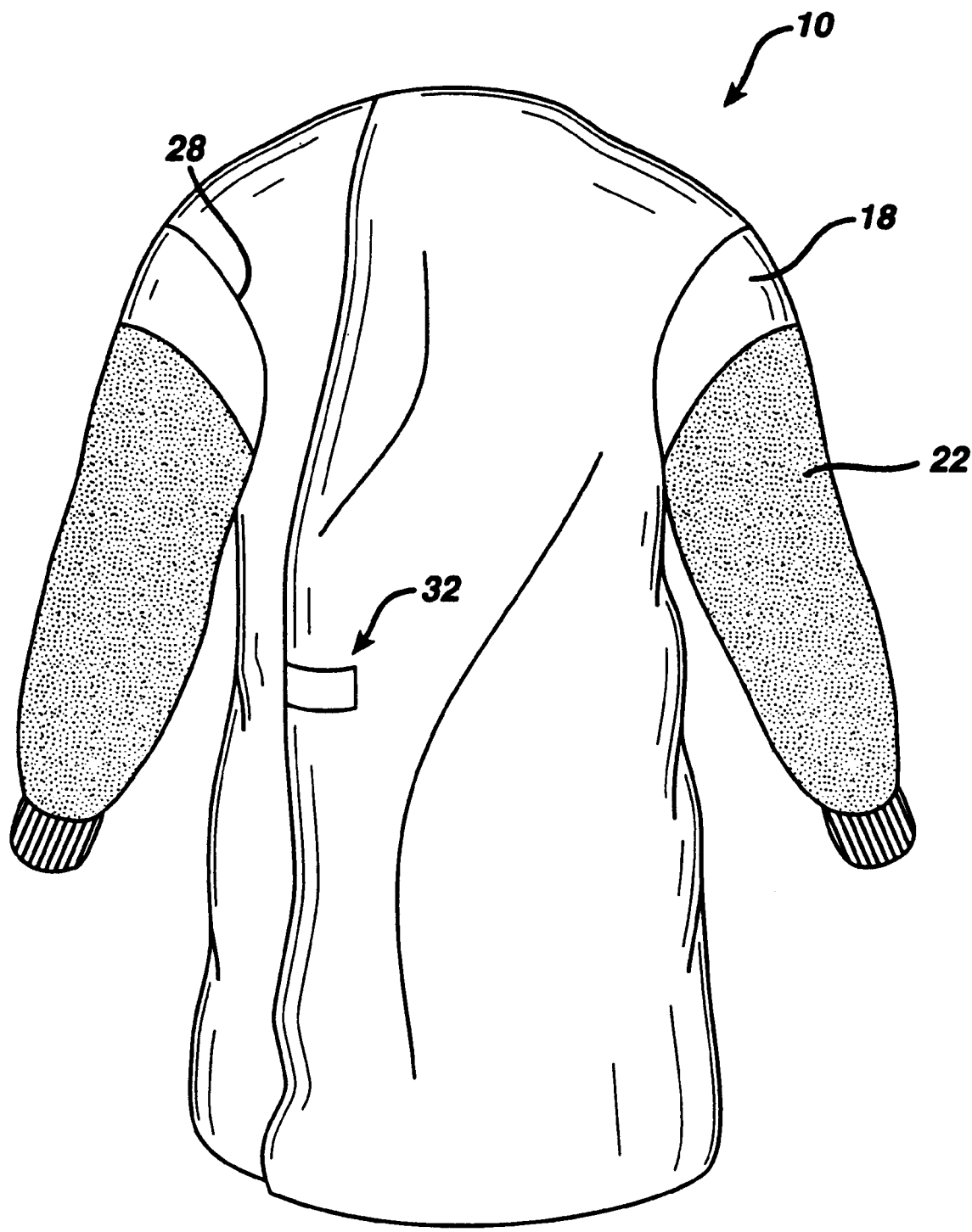
FIG. 11 is a rear elevational view of the gown of FIG. 2, shown closed.

FIGS. 6 to 10 illustrate the procedure for applying the waist closure 32. First, the user grasps tab 60 to remove the release strip 56 from the first adhesive layer 44, as illustrated in FIG. 7. This procedure may be performed with a non-sterile hand and still effect sterile closure of the waist closure 32 as will be illustrated. By holding the tab 60, the first adhesive layer 44 may be properly positioned over the gown back 16 adjacent the second edge 42. By applying pressure at the second indicia 68, such as with a finger, the first adhesive layer 44 is adhered to the gown back 16. Finally, the bi-fold tab 64 is grasped, and the release strip 56 is removed and discarded. During the procedure only the release strip 56, which is discarded, is touched with non-sterile hands. The final closure is illustrated in FIG. 11.

Other treatments may be applied to the underlying fabric to provide regional performance characteristics to a gown, or also to a surgical drape. For instance, some gown and drape applications, for example those used for less wet procedures, do not require complete imperviousness and some lesser levels of water repellency may be adequate. Currently, this is achieved by immersing the entire fabric in a fluorocarbon based repellency agent. The excess liquid is then expressed and the fabric dried. The treatment is repeated to achieve an acceptable level of repellency characterized by a static head of between 20 and 30 cm, preferably about 25 cm.

Using the method of the present invention as an alternative, a water based emulsion of acrylic ester, or other repellency enhancing substance such as a fluorocarbon or silicone, may be printed onto the fabric substrate. On many nonwoven substrates, the preferred dry coating weight for acrylic ester is approximately 2.0 grams per square yard, which corresponds to a coated fabric with a hydrostatic head of 25 cm. One of skill in the art can determine the appropriate coating level to achieve desired levels of repellency with a given fabric substrate and coating material without undue experimentation. Achieving the 25 cm level of repellency does not depend critically on a particularly printing process, and techniques such as rotogravure or flexography which deliver lower coating weights, are suitable. Using the method of the present invention, the emulsion or other repellency enhancing material need only be applied where the added repellency is required. For instance, the back portion 15 of the gown 10 can be made from a rather insubstantial nonwoven fabric with low repellency and yet have its repellency raised in this manner.

It may be desired, especially in the instance of drapes to have an area with enhanced absorption. Currently this is provided by laminating an absorbent layer of material to the fabric of the drape. Such material is capable of absorbing body fluid, such as blood, to create a relatively dry area where a surgeon may more easily work. Instead, according to the present invention, it is possible to print a layer of absorbent material, such as an acrylic acid based superabsorbent, either as a finished polymer or as a water base suspension of the precursor compounds, to a localized region to provide enhanced fluid absorptive capability. Preferably, this would be provided adjacent a fenestration through which surgical procedure is to be performed. Employing any of the well known acid based superabsorbent materials, such a coating would be capable of absorbing a greater volume of liquid than conventional laminated fabric materials. Based upon the present disclosure, other printable absorbent materials will be apparent to those of skill in the art.

Figure 12:
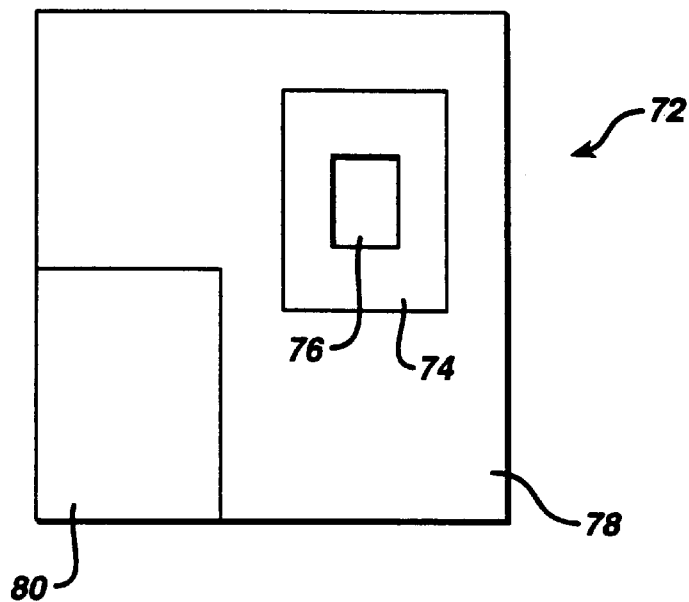
FIG. 12 is a plan view of a drape according to the present invention, shown prior to assembly.
Figure 13:
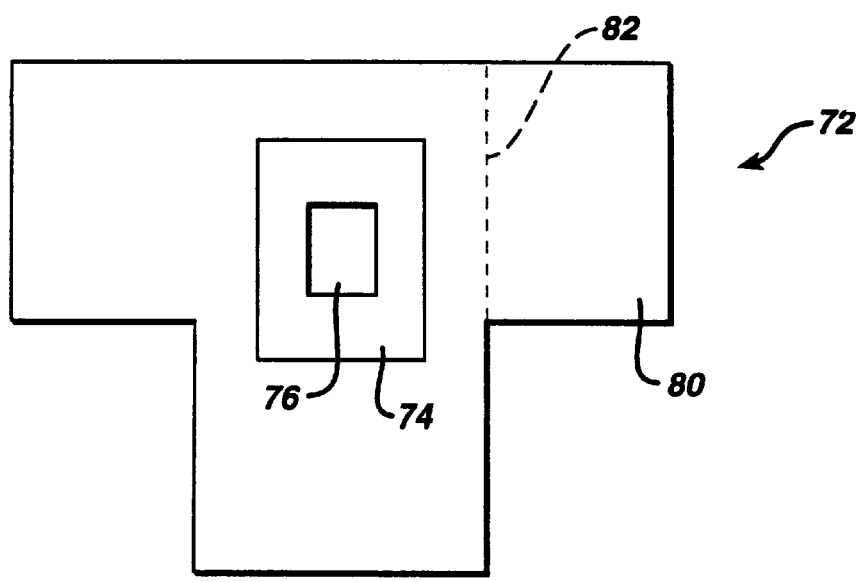
FIG. 13 is a plan view of the assembled drape of FIG. 12.

FIGS. 12 and 13 illustrate a T-shaped (a common drape configuration) drape 72 having a region of enhanced absorption 74 printed thereon about a fenestration 76 therethrough. FIG. 12 illustrates the drape 72 prior to assembly. A rectangular sheet 80 of a non-woven fabric has the area of enhanced absorption 74 printed thereon at the fenestration 76. A rectangular corner 80 is cut from the sheet 78. FIG. 13 illustrates the drape 72 with the corner 80 attached to a side edge 82 of the sheet 78 to form the T configuration.

It may also be desirable to enhance friction in certain regions of a drape or gown. For instance drapes sometimes carry a thin layer of open cell foam located adjacent to incision cite. This material has a high coefficient of friction and the surgeon is able to place his instruments on the pad with the certainty that irrespective of the angle, the item will not slip. A similar effect can be achieved using a printed film of polyvinyl chloride plastisol containing a high concentration of non-migratory plastisol-trimellitate ester. When the solvent has been driven off and the plastisol cured, the resulting film has an extremely high level of tack and behaves in a way similar to a conventional foam instrument pad. Such a high tack coating, on a fabric base, can also be used as a liner for an instrument tray. Other tack enhancing coatings will be apparent to those of skill in the art.

The performance enhancing coating can be applied to the fabric substrate in any appropriate manner. A fluid coating material is applied and adhered to the substrate. The fluid may comprise the performance enhancing material dissolved in a solvent, or mixed into a suspension with a liquid carrier, in which case the solvent or carrier will typically be evaporated or otherwise at least partially removed to fix the material to the substrate. Alternatively, the fluid material may comprise a granular flowable powder of the material, in which case it may be fixed to the substrate electrostatically, or by fusion. Any conventional printing or spray coating method may be employed as long as there is some way to control where the coating will be applied so as to coat distinct regions of the substrate. Other methods for adhering a fluid coating to the substrate will be apparent to those of skill in the art.

Figure 14:
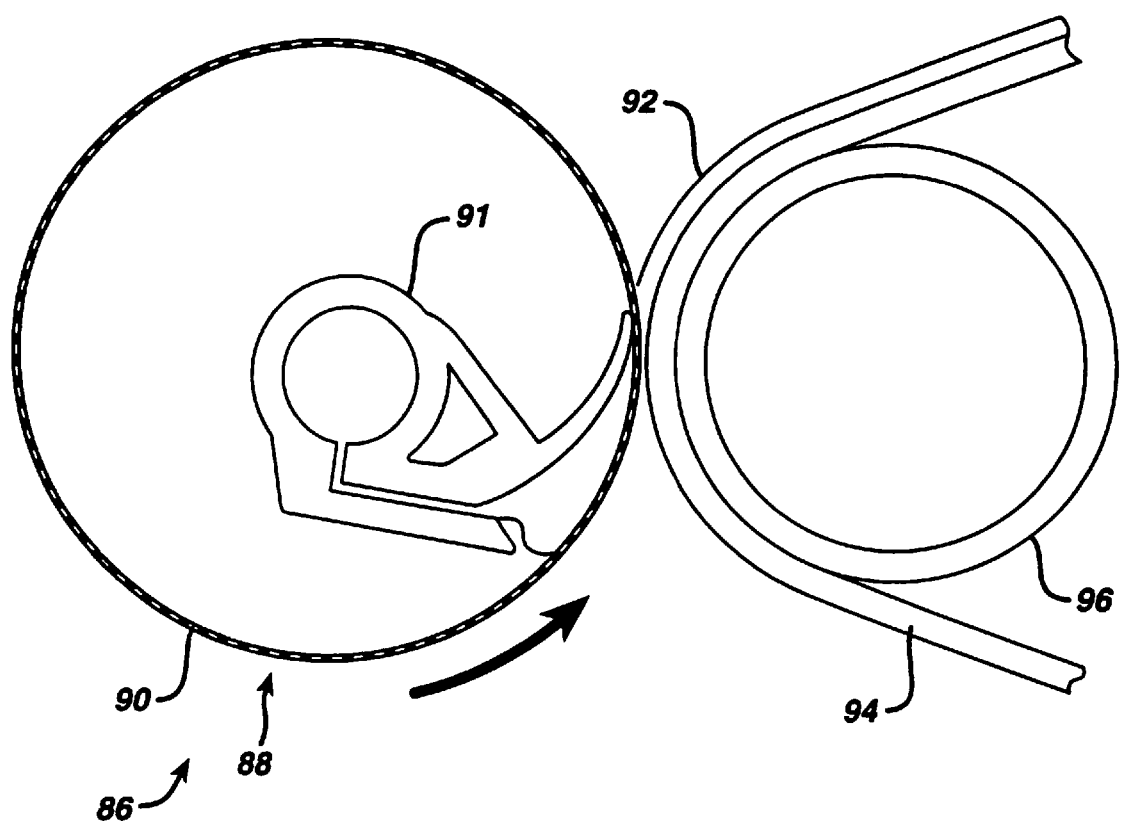
FIG. 14 is a sectional view of a rotary screen printer for printing performance enhancing materials onto selected regions of medical linens according to the present invention.

FIG. 14 illustrates a rotary screen printing mechanism 86 suitable for applying performance-enhancing coatings. It comprises a rotating drum 88 having perforations 90 therethrough in a pattern adapted to print the predetermined design. A squeegee 91 inside the drum 88 forces a flowable coating material 92 through the perforations 90 where they exist to apply a pattern of the coating material 92 onto a fabric substrate 94. The substrate 94 passes over a roll 96, which may be driven, and which places the substrate 94 into contact with the drum 88.

Figure 15:
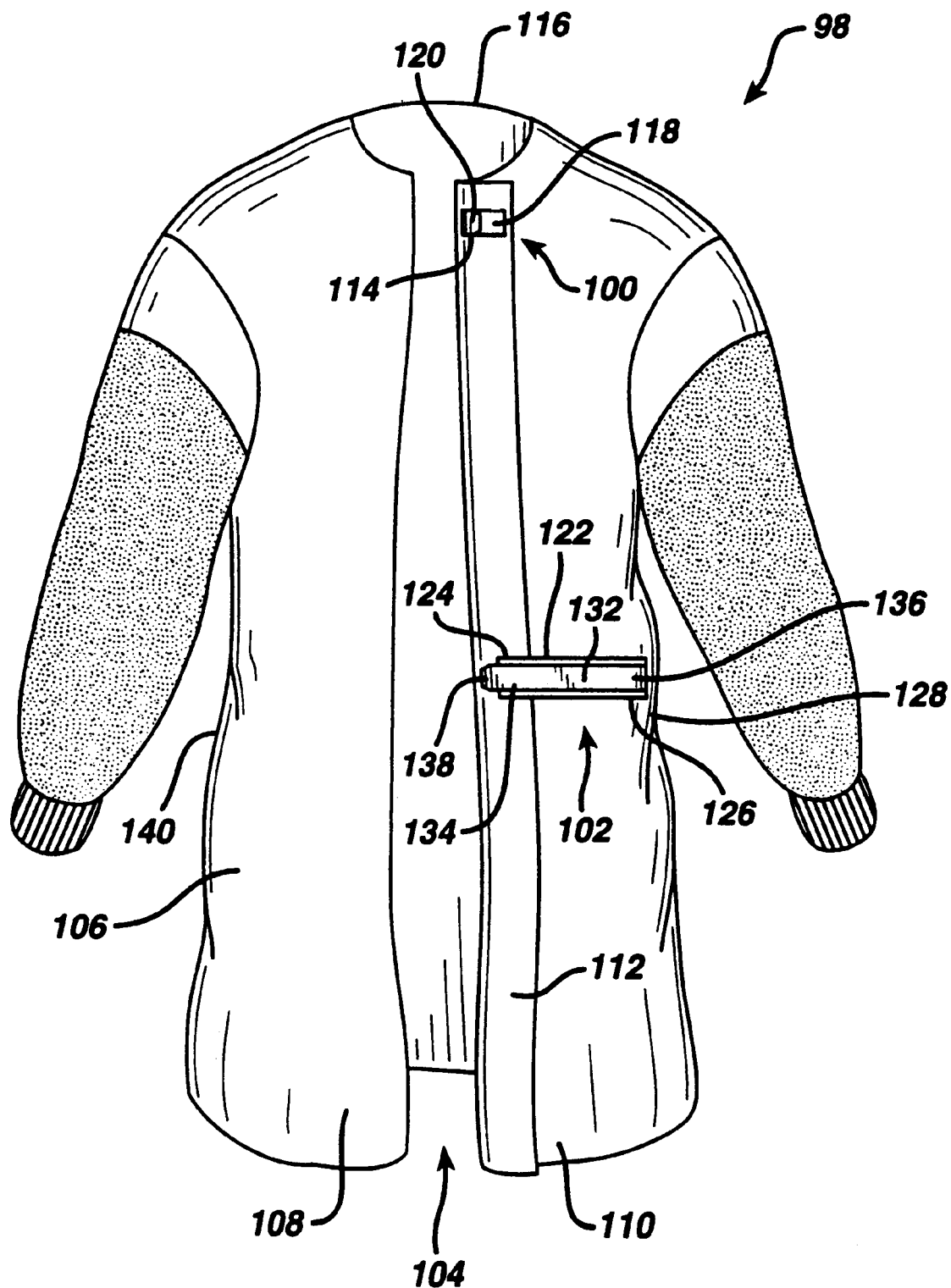
FIG. 15 is a rear elevational view of a further embodiment of a gown according to the present invention.

FIG. 15 illustrates a gown 98 having alternative neck and waist closures 100 and 102. An opening 104 extends up the back 106 of the gown to provide left and right back panels 108 and 110. The right back panel 110 is folded over outwardly along its length forming a flap 112. A region of adhesive 114 is provided on the flap 112 near the gown's neck 116. This may be printed thereon, preferably simultaneously or contemporaneously with the repellent coatings to speed construction of the gown 98, or may comprise a double-faced tape. A release liner 118 with a free-end tab 120 covers the adhesive 114. The neck closure 100 operates by removing the release liner 118 by means of the tab 120 and then folding the flap 112 at the region of the adhesive 114 over onto the left back panel 108 where the adhesive 114 adheres the two back panels 108 and 110 together. See also FIG. 21. Another manner in which the tab may function, places the adhesive on the tab, with the tab being opened away from the body and then attached to the body across the opening 104

The waist closure 102 has a pass-off feature which achieves an effect similar to pass-off cards used on some surgical gowns with ties at the waist. With these gowns, the ties are attached to a card which is passed by a wearer to an assistant, who need not be sterile, merely clean. The assistant then passes one of the ties around the wearer's torso touching only the card. The wearer then grasps the tie and the non-sterile card is removed.

The closure 102 comprises a strip 122, which preferably is formed of the same material as the gown 98, and which extends laterally from a first end 124 thereof attached to the flap 112 to a second end 126 attached at the side 128 of the gown 98. A face 130 of the strip 122 which faces outwardly bears an adhesive with a release liner 132 thereover. The release liner similarly has a first end 134 and a second end 136, corresponding to the strip first and second ends 124 and 126. The release liner first end 134 extends slightly from the adhesive to form a tab 138 and the second end 136 is releasably attached to the strip second end 126, but with significantly greater force than the attraction between the adhesive and the release liner 132. For instance, it may be physically attached thereto, such as with a stronger bond adhesive or thermal bonding.

Figure 20:
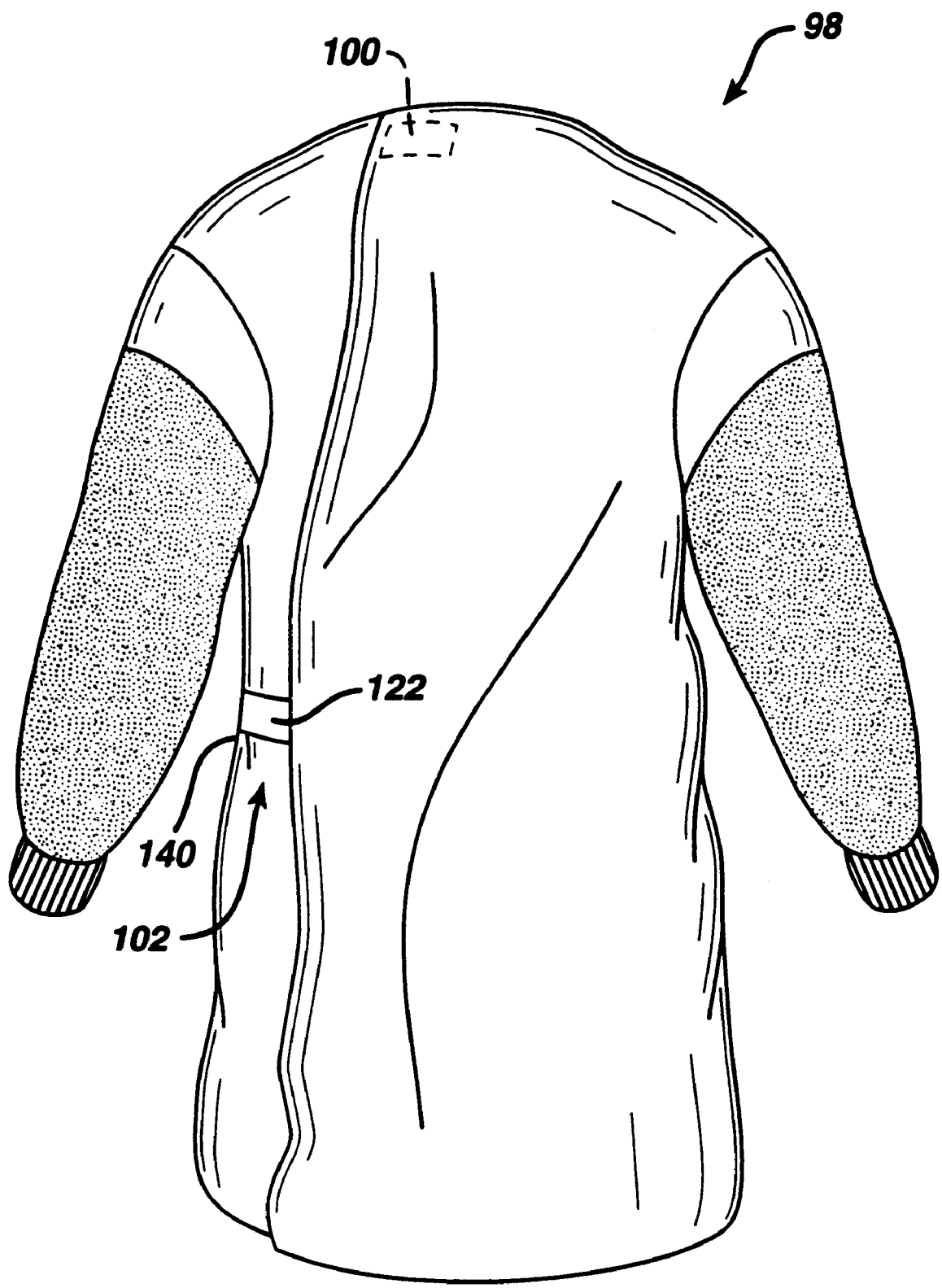
FIG. 20 is a rear elevational view of the gown of FIG. 15 shown closed.

FIGS. 16 to 19, illustrate operation of the closure 102. First, the wearer's assistant grasps the tab 138 and lifts the release liner 132 away from the strip 122, except where the two join at their second ends 126 and 136. While holding only the release liner 132, the assistant passes the strip second end 126 behind the wearer's back to a location 140 at the side or front of the gown 98. The wearer, with sterile hands, presses only against the strip 122 to adhere the strip 122 to the gown 98 and effect closure. The assistant then removes the release liner 132. The wearer never touches the release liner 132, and the assistant touches only the release liner 132. FIG. 20 shows the closed gown 98 and FIG. 21 illustrates the neck closure 100, described above, in more detail. In any of the adhesive closures, an acrylic adhesive is preferred, but substitutions therefor will be apparent to those of skill in the art. Such substitutions could also include hook and loop closures.

Various modifications and alterations of this invention will be apparent to those skilled in the art without departing from the scope and spirit of this invention. It should be understood that the invention is not limited to the embodiments disclosed herein, and that the claims should be interpreted as broadly as the prior art allows. For instance those of skill in the art can find suitable alternatives to the specific performance enhancing coatings described herein without undue experimentation.

What is claimed is:

1. A medical linen comprising:

a fabric substrate; and a coating printed on one or more regions of the substrate, but not the entire substrate, said coating modifying a performance characteristic of the fabric substrate.

2. A medical linen according to claim 1 selected from the group consisting of: a medical gown and a medical drape.

3. A medical linen according to claim 1 wherein the substrate comprises a nonwoven fabric.

4. A medical linen according to claim 1 wherein the coating modifies the performance of the substrate in a manner selected from the list consisting of: increasing the liquid repellency of the substrate, increasing the friction of the substrate and enhancing the liquid absorbing capacity of the substrate.

5. A medical linen according to claim 1 comprising a medical gown comprising a body covering portion and sleeves extending from the body portion to terminate in cuffs, wherein said one or more regions comprises a central operative area of said body covering portion and further comprises portions of said sleeves adjacent said cuffs and wherein said coating is liquid impervious.

6. A medical linen according to claim 5 wherein said coating comprises polyvinylchloride plastisol.

7. A medical linen according to claim 5 wherein the gown further comprises one or more areas coated with a repellency enhancing material to raise the repellency in said one or more areas to at least 20 cm of static head.

8. A medical linen according to claim 1 comprising a medical drape having a fenestration therethrough.

9. A medical linen according to claim 8 wherein the coating absorbs water and is positioned adjacent the fenestration.

10. A medical linen according to claim 9 wherein the coating comprises an acrylic acid based absorbent material.

\* \* \* \* \*